United States Patent [19]
Regan

[11] 4,012,128
[45] Mar. 15, 1977

[54] METHOD AND APPARATUS FOR DETERMINING VISUAL LATENCY

[75] Inventor: David Regan, Newcastle-under-Lyme, England

[73] Assignee: Wilkinson Sword Limited, England

[22] Filed: May 23, 1975

[21] Appl. No.: 580,474

[30] Foreign Application Priority Data

June 7, 1974 United Kingdom ............ 25352/74

[52] U.S. Cl. .................................. 351/17; 351/23; 351/31; 351/36; 351/37; 351/39
[51] Int. Cl.² ......................................... A61B 3/02
[58] Field of Search ................... 351/17, 23, 24, 30, 351/31, 36, 37, 39

[56] References Cited

UNITED STATES PATENTS

| 2,495,708 | 1/1950 | Draeger et al. ................. 351/17 X |
| 3,473,868 | 10/1969 | Young et al. ........................ 351/6 |

OTHER PUBLICATIONS

Bryngdahl, JOSA, "Characteristics . . . Region," vol. 56, No. 6, pp. 811–815, 6/1966.

Cohn et al., "Techniques, Instruments, Cases," Am. J. Optom. and Phys. Optics, vol. 51, 12/1974, pp. 993–997.
Lichtenstein et al., "Relative . . . Latency . . .," JOSA, vol. 51, pp. 1033–1034, No. 9, 1961.

Primary Examiner—Paul A. Sacher
Attorney, Agent, or Firm—Leydig, Voit, Osann, Mayer & Holt, Ltd.

[57] ABSTRACT

Apparatus and methods for testing temporal resolution of vision in a human subject are disclosed in which a light source is repetitively energized to produce pairs of visual stimuli, and the time interval between two stimuli in each pair is varied so as to enable the assessment of the minimum interval for which the subject under test can discern the separate stimuli in the pair. Means are provided for fixating the center of the subject's visual field, and the position of the visual stimuli within the visual field is varied so as to enable a map to be drawn showing the variation of the subject's temporal resolution over his visual field. Temporal resolution measured in this way enables certain diseases to be diagnosed and distinguished.

31 Claims, 12 Drawing Figures

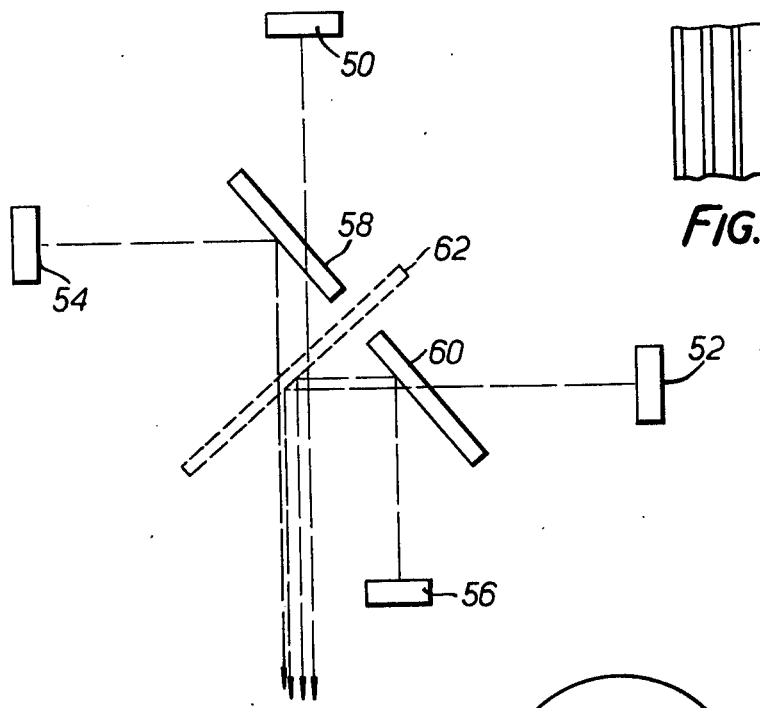
FIG.4.
FIG.5.
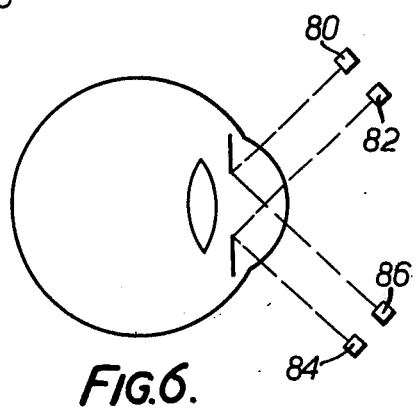
FIG.6.
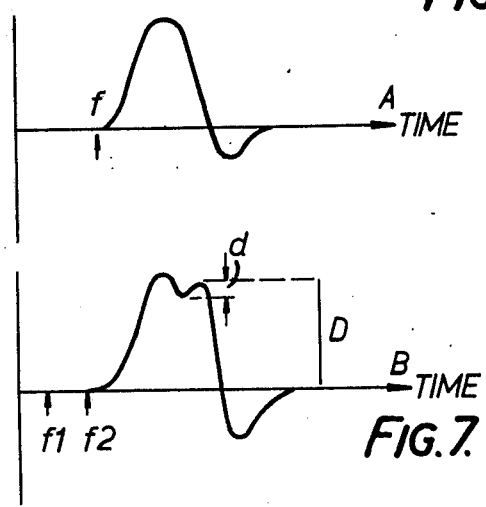
FIG.7.

4,012,128

METHOD AND APPARATUS FOR DETERMINING VISUAL LATENCY

BACKGROUND OF THE INVENTION

The invention relates to vision testing apparatus and methods and more particularly to apparatus and methods for testing temporal resolution of vision in a human subject. Temporal resolution of vision is a measure of the patient's ability to perceive rapid temporal variations in some aspect of visual stimulus.

It has now been found that measurement of temporal resolution of vision enables detection and diagnosis of certain diseases such as multiple sclerosis and others. Assessment of temporal resolution of vision is also important in assessing the adequacy of vision when testing the ability of a subject to cope with certain oculomotor or recognition tasks. In these connections, it has also been found advantageous to be able to prepare a map showing how the subject's temporal resolution varies over his visual field.

An object of the invention is therefore to provide improved apparatus and methods for measuring temporal resolution in a human subject.

Another object of the invention is to provide improved methods and apparatus for measuring the variations of temporal resolution in a subject's visual field.

BRIEF SUMMARY OF THE INVENTION

According to the invention, there is provided a method of testing vision, including the steps of repetitively producing a group of visual stimuli containing a predetermined number of successive stimuli, varying the time intervals between the stimuli in each group, and assessing the minimum interval for which the subject under test can discern the separate stimuli.

According to the invention, there is also provided a method of testing vision, comprising the steps of producing a visual stimulus of periodically varying intensity for a small discrete portion of a subject's visual field, changing the amplitude of the intensity variations, and assessing the minimum amplitude value for which the subject can discern the variations.

According to the invention, there is further provided apparatus for testing vision, including visual stimulus means, activating means connected to the visual stimulus means and repetitively operative to produce therefrom a group of visual stimuli containing a predetermined number of successive stimuli, and control means connected to the activating means to vary the time intervals between the stimuli in each group so as to enable the minimum interval discernible by a subject under test to be assessed.

According to the invention, there is yet further provided apparatus for testing vision, comprising fixation means for fixating the subject's visual field, light source means for producing a small discrete visual stimulus in a portion of the visual field, first control means for giving the visual stimulus a periodically varying intensity, and second control means for changing the amplitude of the intensity variations to assess the minimum amplitude value for which the subject can discern the variations.

BRIEF DESCRIPTION OF THE DRAWINGS

Apparatus embodying the invention, and methods employing the invention, for testing temporal resolution of vision, will now be described, by way of example only, with reference to the accompanying diagrammatic drawings in which:

FIG. 4 is a diagrammatic view of another form of the apparatus;
FIG. 5 is a diagrammatic front view of part of the apparatus of FIG. 4;
FIG. 6 is a diagrammatic view showing pupillary diameter measuring apparatus which can be used with the apparatus of FIGS. 1 to 3 or 4 and 5;
FIGS. 7a and 7b are waveforms produced by the apparatus of FIG. 6.

DESCRIPTION OF PREFERRED EMBODIMENTS

The apparatus and method to be described may be used in association with, though are distinct from, the apparatus and methods disclosed in my related patent application Ser. No. 328780 now U.S. Pat. No. 3,837,734.

Figure 1:
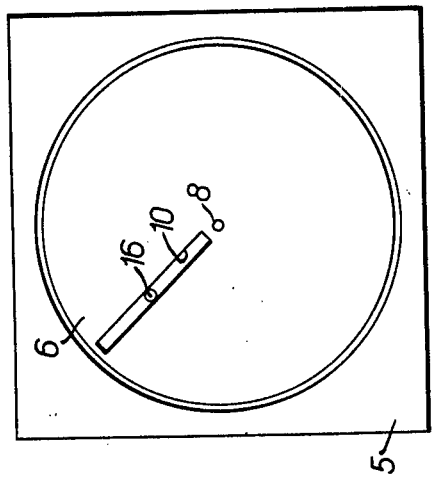
FIG. 1 is a front view of the apparatus.

As shown in FIG. 1, the apparatus comprises a cabinet 5 in the front face of which is rotatably mounted a matt white disc 6 which may, for example, be about two feet in diameter which can be set into any angular position over 360°. At the center of the disc is mounted a lamp 8 or other visible mark. In certain cases (for example where it is desired to test the adequacy of vision under conditions of poor light) it may be desirable for the disc 6 to be matt black.

Figure 2:
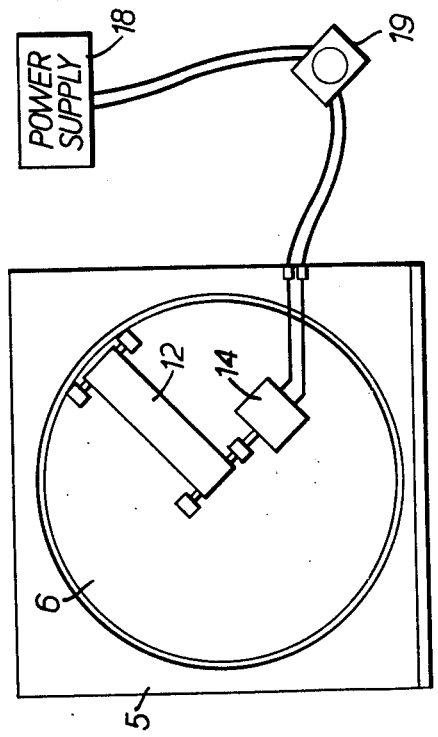
FIG. 2 is a rear view of the apparatus of FIG. 1.

The disc 6 has a radially extending slot 10, and as shown in FIG. 2, a continuous band 12 is mounted on the rear of the disc so that one of its runs covers the slot 10. An electric motor 14 is connected to one of the rollers, over which the band 12 runs, and can be operated to drive the band in either direction.

The band carries a second lamp 16 (FIG. 1) which is preferably of the solid state type as is lamp 8. Such a light source has the advantage of fast-rise time and fast-decay time so that it can be switched on and off abruptly. Furthermore, its maximum (or minimum) intensity can be easily controlled by electronic means.

As shown diagrammatically in FIG. 2 (but omitted from FIG. 1), the motor is energised from a power supply 18 under control of a remote hand-held switch 19. The switch enables the motor to be run in either direction. In this way, the lamp 16 can be moved to any radial position relative to the lamp 8, and simultaneous angular re-positioning of the disc 6 thereby enables the lamp 16 to be placed in any position within the area defined by the disc periphery.

Instead, the motor and moving band can be omitted and the lamp 16 mounted in a radial slot so that it can be radially moved by hand. In either case, the source 16 and the background provided by the disc 6 are and always remain immediately contiguous.

Figure 3:
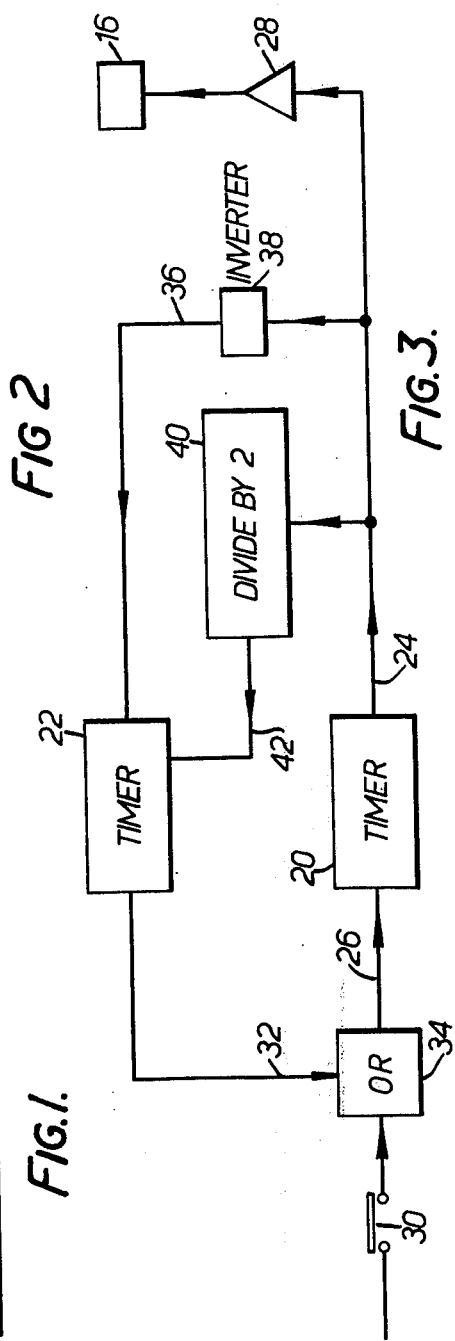
FIG. 3 is a block circuit diagram of the apparatus of FIGS. 1 and 2.
Figure 8:
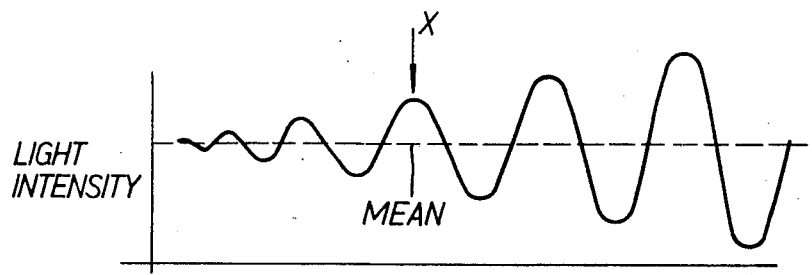
FIGS. 8 to 11 are waveforms of light intensity occurring in a modified form of the apparatus of FIGS. 1 to 3.
Figure 9:
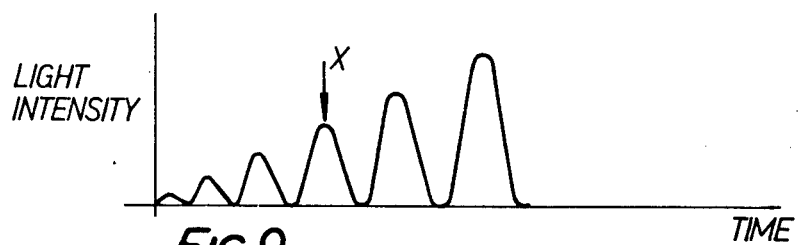
Figure 10:
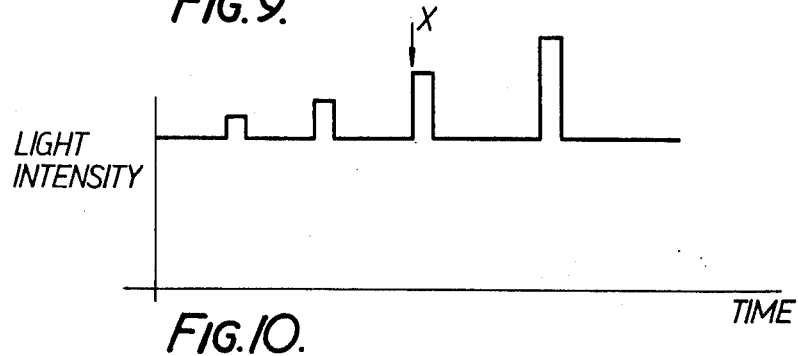
Figure 11:
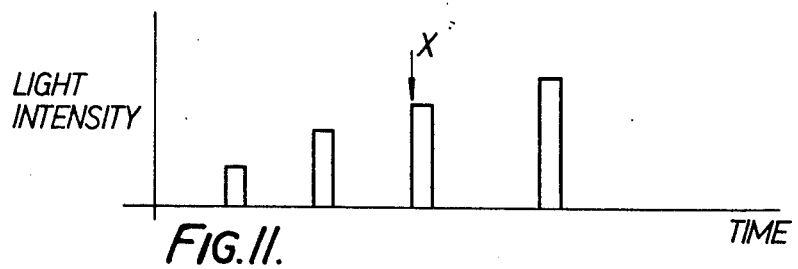

FIG. 3 shows the circuit diagram for driving the lamp 16. The circuit diagram comprises two electronic timing units 20 and 22. Timer 20 has an output line 24 which becomes energised when the timer receives an INITIATE signal on a line 26 and becomes de-energised at the end of the pre-set period of the timer. The line 24 drives the lamp 16 through an amplifier 28.

The line 26 is energised from a push button switch 30 or from an output line 32 of timer 22, via an OR gate 34. Line 32 becomes energised at a pre-set time after timer 22 has been initiated, this pre-set time being the pre-set period of the timer. Timer 22 is energised via a line 36 which is connected to line 24 through an inverter 38. In this way, timer 22 is initiated when line 24 becomes deenergised at the end of the pre-set period of timer 20.

A divide-by-two counter 40 senses the operations of the timer 20 and energises an INHIBIT line 42 on every second initiation of timer 20. When energised, line 42 prevents initiation of the timer 22 by the line 36.

During the test, the patient positions himself in front of the disc 6 and maintains his gaze continuously and accurately on the fixation light or mark 8. The patient is positioned so that his visual field encompasses the area of the disc. The disc 6 is illuminated either from the front or rear at a constant and standard level of light throughout the test. The operator then rotates the disc 6 and operates the motor 14 so as to position the lamp 16 at a desired position in the patient's visual field. The operator then presses the push button 30 so as to initiate timer 20. Line 24 becomes energised and illuminates the lamp 16 for a preset period (say, 10mS). At the end of this period, lamp 16 is abruptly de-energised and timer 22 becomes energised. At the end of the pre-set period of timer 22, line 32 is energised and re-initiates timer 20. Once again, therefore, lamp 16 is illuminated for the pre-set period of the timer 20. The second initiation of timer 20 is detected by the divider unit 40 which energises the INHIBIT line 42 to prevent subsequent operation of timer 22.

In this way, lamp 16 is flashed twice, with the length of each flash being controlled by the timer 20 and the length of the interval between the two flashes controlled by the timer 22.

This test is repeated with the length of the interval between the flashes varied for each test, and for each test the patient is asked whether he can distinguish the two flashes of each test. In this way, the largest interval for which the patient is just unable to distinguish the flashes as double is obtained.

Therefore, the patient's temporal resolution of vision is being tested as his ability to perceive light stimuli that are physically separated in time as being so separated.

The lamp 16 is then moved to a different position in the patient's visual field, and the series of test repeated; and so on for other positions in the visual field.

The test procedure is then repeated for the patient's other eye, and in this way, a map of the patient's temporal resolution can be drawn up showing the variation of the patient's temporal resolution over his visual field.

It is found that multiple sclerosis degrades the temporal resolution of vision. Measurement of the temporal resolution in the described way, and its variation over the field of vision, can therefore give a sensitive indication of visual pathology in multiple sclerosis, even in those cases (which may well occur) where visual activity is not otherwise affected or is only fleetingly affected and even when there is no history of classical visual signs or symptoms. The apparatus and method described can also offer assistance in discriminating between multiple sclerosis and other diseases in patients.

However, the apparatus and method described are not restricted to diagnosis and study of multiple sclerosis. They may also be of use in the investigation of retrobulbar neuritis, colour blindness and opthalmological defects such as amblyopia and glaucoma, and in assessing the adequacy of vision for the performance of oculomotor or recognition tasks which require good temporal resolution (for example, for drivers, pilots or operators of machinery).

A number of modifications can be made to the apparatus and method of FIGS. 1 to 3.

In one modification, the lamp 16 is not mounted to be movable within the subject's visual field. Instead, the lamp 8 (or other means providing the fixation mark) is physically moved to give the effect of moving the lamp 16 within the visual field. Instead, the lamp 16 may remain fixed at the centre of the visual field, to test the overall temporal resolution.

In another modification, the circuitry is modified so that the lamp 16 is normally on but is switched off by the timer 20. Each test in this case therefore consists of two short periods for which the lamp 16 is off, separated by a period for which it is on, and the latter period is varied in length so as to find the largest interval for which the patient is just unable to distinguish the two off-periods.

In a further modification, the lamp 16 is modified so that each flash-presentation is a presentation of a spatially-patterned stimulus. For example, the light source 16 might present a pair of flash-presentations of a checkerboard or grating pattern. Again, the largest interval between the presentations for which the patient is just unable to distinguish that the pattern appears twice, is found.

In another modification, the light source 16 is sometimes a spatially-unpatterned area of light and at other times a spatially-unpatterned area. However, the total light flux emitted by the stimulus and its mean luminance does not change. The light source may, for example, be spatially-unpatterned for most of the time so as to present a constantly lit area in the visual field. This area then changes to a patterned appearance (e.g. a pattern of stripes) and remains so patterned for a period controlled by a timer corresponding to timer 20 (FIG.3). It then reverts to the unpatterned constantly lit form for a period controlled by a timer corresponding to timer 22 and then reappears with the patterned appearance for a second time period controlled by the timer corresponding to timer 20. The largest interval is found for which the patient is just unable to distinguish that the pattern appears twice. This type of test may be reversed by arranging for the light source to present a spatially-patterned area for most of the time and then to become spatially unpatterned for two controlled periods which are separated by a controlled period for which the lit area is again spatially patterned. These two modifications may be carried out using a cathode ray tube (CRT) to provide the unpatterned and spatially patterned area (by electronically controlling the modulation of the brightness). The CRT may be positioned in the centre of the subject's visual field to test his overall temporal resolution. Instead, it may be a miniature CRT positioned eccentrically on a controlled background whose centre is defined by a fixation mark or light which is movable from the centre to alter the apparent position of the CRT in the subject's visual field. In carrying out these two modified test procedures, series of tests may be carried out at different levels of brightness and/or contrast for the pattern.

In another modification, the luminance contrast of the stimulus does not change at any time. For most of the time, the stimulus light is a spatially-unpatterned patch of uniform colour. For a period controlled by a timer corresponding to the timer 20 (FIG.3), the stimulus then changes into a spatial pattern where adjacent areas are distinguished by their different colours. After a time period controlled by a timer corresponding to timer 22 (FIG.3), the stimulus again changes into such a pattern for a period controlled by the time corresponding to the timer 20. A series of tests is carried out in which the largest interval is found for which the subject is just unable to distinguish the doubleness of the appearance of the pattern. FIGS. 4 and 5 show one example of apparatus which may be used to implement this modification.

The apparatus (FIG.4) comprises a first source 50 of red light, a second source 52 of red light, a first source 54 of green light, and a second source 56 of green light. The sources 50 and 52 are positioned to transmit their red light beams through respective beam splitters 58 and 60 to a patterned mirror 62, the reflecting portions on which are arranged in parallel stripes of which a portion is shown diagrammatically in FIG. 5. That part of the red light from the source 50 which passes between the reflecting stripes of the mirror 62 travels onwards towards the subject's eye shown at 64. The red light from the source 52 reaches the subject by reflection from the reflecting stripes of the mirror 62.

The green light from the sources 54 and 56 reaches the mirror 62 by reflection from the beam splitters 58 and 60. The green light from the source 54 which passes between the stripes of the mirror 62 is directed towards the subject, as does the green light from the source 56 which is reflected by the stripes of the mirror 62.

In operation, for most of the time all four light sources are arranged to produce light of equal luminance. The composite light beam reaching the subject 64 is therefore made up of regularly spaced beams of red and green light of equal luminance, and the result is that the subject sees a yellow area.

For a period controlled by a timer corresponding to the timer 20 of FIG. 1, the luminance of the red light from the source 50 is given a step increase and the luminance of the red light from the source 52 is given an equal step decrease. Simultaneously with this, the green light from the source 54 is given a step decrease and the green light from the source 56 is given an equal step increase. The overall result is that neither the mean luminance nor the luminance at any point of the mirror seen by the subject has changed, but because of the changes in the luminance of adjacent beams reaching the subject's eye, he now sees a spatial pattern of alternating red and green eyes. The light beams then revert to equal luminance for a period controlled by the timer corresponding to timer 22, and then once more undergo the step changes in luminance for a period controlled by the timer corresponding to timer 20. At the end of this period they then revert to equal luminance. As explained, a series of tests is carried out in which the largest interval is found for which the patient is just unable to distinguish the doubleness of the appearance of the pattern.

The apparatus of FIG. 4 may be arranged to produce the composite output beam through a small area of a suitable background sheet which the subject views. The effective position of the composite beam in the subject's visual field can be altered by moving a fixation mark or light over the sheet.

In a modification, the operation of the apparatus of FIGS. 4 and 5 is reversed so that the stimulus light beam is spatially patterned for most of the time, with adjacent areas distinguished by different colours, and then briefly becomes unpatterned for the two successive periods of time, with the mean luminance maintained constant.

Tests of the form described above in which the stimuli switch between spatially patterned and spatially unpatterned forms provide particularly effective testing of the transmission of nerve signals relating to edge detection and pattern vision.

In any of the tests, it is advantageous that the test procedure used be such as to minimise the effects of changes in the patient's criterion of judgement. One such procedure is the psychophysical method of ascending and descending limits. Thus, the length of the time interval between the double stimuli could be gradually decreased until the subject has indicated that he no longer observes the stimuli as separate. The series of tests is then repeated but with the time interval gradually increased from a very low level until the patient has indicated that he can observe the two stimuli as being separate.

Another psychophysical method which could be used is the method of constant stimuli. Here, tests are carried out in which the two stimuli have various ones of a number of different preselected time intervals between them and for each test the patient is asked to indicate whether or not he can observe the stimuli as being separate. When, for a particular time interval, for example 50% of the subject's answers indicate that he observes the stimuli as being distinct and 50% of his answers indicate that they are not distinct, this particular time interval can be taken as the time interval to be determined.

FIGS. 6 and 7 show apparatus by which the patient's response is measured objectively rather than subjectively. It is found that the diameter of the patient's eye pupil changes in response to each of the pair of light stimuli in each test, but the pupillary response is no longer double when the interval between the successive visual stimuli is less than a certain value. This value gives an index of the visual pathways temporal resolution. Besides the advantage of objectivity, this procedure has the advantage that the measurement obtained of temporal resolution is not affected by the conditions of the fibres in the retino-calcarine pathway central to the lateral geniculate body.

As shown in FIG. 6, two sources 80 and 82 of radiation (which may be visible radiation or, for example, infra-red radiation) are positioned so as to direct radiation upon diametrically-opposed edges of the patient's pupil. Two photocells 84 and 86 are mounted so as to receive radiation reflected by the eye from the radiation sources 80 and 82. The photocells 84 and 86 are electronically connected additively. Since radiation is reflected only by the iris and not by the pupil, the summed output from the additively connected photocells will indicate changes in pupillary diameter.

In operation, the apparatus of FIG. 6 can be used in conjunction with that of FIGS. 1 to 3. The patient is positioned so as to fixate on the lamp fixation mark 8 on the disc 6, and with the radiation sources 80 and 82 and the photocells 84 and 86 correctly positioned to detect changes in his pupillary diameter in the eye under test. A series of tests is then carried out in the manner explained in connection with FIGS. 1 to 3, and for each test the output of the differentially connected photocells is observed such as by means of a CRT.

FIG. 7A shows the photocell output plotted against time for a single, brief, light flash occurring at a time $f$. FIG. 7B shows a hypothetical response to a pair of light flashes $f_1$ and $f_2$. Here, a double peak can be seen in the response. If the ratio d/D (see FIG. 7B) exceeds a predetermined limit, then the patient's iris can be said to have responded separately to the two flashes. When the magnitudes of the double peak are below this predetermined limit, then the iris response is considered not to have distinguished the two separate stimuli. The ratio of d/D can be taken as a measure of the temporal resolution.

If the signal-to-noise ratio at the photocells 84 and 86 is too low, then it may be necessary to enhance the signal-to-noise ratio by taking into account the results of stimulating the eye with not one but many pairs of flashes for each test. For example, the output from the photodetectors could be fed to a non-adaptive cross-correlator (e.g. an averaging or summation device) which would also receive signals directly synchronised with the light stimuli. The correlator operates by suppressing those signals from the photodetectors which are not systematically related in time to the light stimuli. The correlator therefore produces output signals each of which can be assumed to be indicative of signals within the optic nerve produced by each stimulus.

The apparatus of FIGS. 6 and 7 can be used in conjunction with the apparatus of FIGS. 4 and 5 if desired.

The methods and apparatus described above can be modified so that each sequence of visual stimuli consists not merely of a pair of successive stimuli but of a group containing a greater but still predetermined number of successive stimuli, the intervals between the successive stimuli in each group being varied to enable the minimum interval for which the subject just discerns the stimuli as separate to be assessed. With more than two stimuli in each group, the effect of the temporal structure of the stimulus sequence on the subject's temporal resolution can be assessed.

In a modification to the apparatus of FIGS. 1 to 3, a switch may be provided in the lead to the lamp 16 to disconnect it temporarily from the circuit of FIG. 3 and to connect it instead to a source of energisation which causes it to emit a light output whose intensity oscillates sinusoidally. The frequency, the amplitude, and the mean intensity can all be arranged to be variable and for each position of the lamp 16 within the subject's visual field, the modulation depth (percentage change in the mean light intensity per modulation cycle) at which the subject just detects the light flicker is determined. When the number of successive stimuli is rendered large and indeterminate in this way (in contrast to the previously described methods in which the number of successive stimuli in each group was small and predetermined), then a graph of modulation depth (at which the subject just discriminates individual flickers) plotted against the reciprocal of the interflicker interval may be referred to as the modulation transfer function. The modified apparatus therefore enables the modulation transfer function to be measured for a discrete and small (10 minutes to 1° of arc for example) portion of the subject's visual field. The modulation transfer function reveals delays mainly caused at a peripheral level in the visual pathway, whereas the device described in the above-mentioned related Patent Application lumps together delays caused at both peripheral and central levels of the visual pathways. If the modulation transfer function is plotted for different values of mean intensity and frequency, further information may be obtainable. For example, if there is a peak in the plot so obtained, this may give information about the lateral inhibitory nerve connections which underlie pattern vision and may be deranged by the diseases mentioned above; these connections determine the extent by which the photoreceptor cells spaced from a visual edge on the retina reinforce the signals developed by the photoreceptors immediately adjacent the edge. Measurement of modulation transfer function therefore provides additional information and the two types of measurement can be used in combination to give improved diagnosis and knowledge of the diseases mentioned above.

It will be appreciated that measurement of modulation transfer function as described above differs from the time delay measurements described earlier in that it maintains a constant light intensity. Therefore, the local state of adaptation of the retina is constant. However, measurements may be extended to cover te case where the minimum intensity is zero. The use of the sinusoidal waveform is advantageous in that it of course contains only one frequency component so that each test frequency is exactly specified. However, if desired, the modulation waveform can instead have rectangular or other desired shape.

FIGS. 8 to 11 show exemplary waveforms of light intensity plotted against time which can occur in the measurement of modulation transfer function. In each of these waveforms, the point where the subject is assumed to first distinguish the flicker is indicated by "X".

Figure 12:
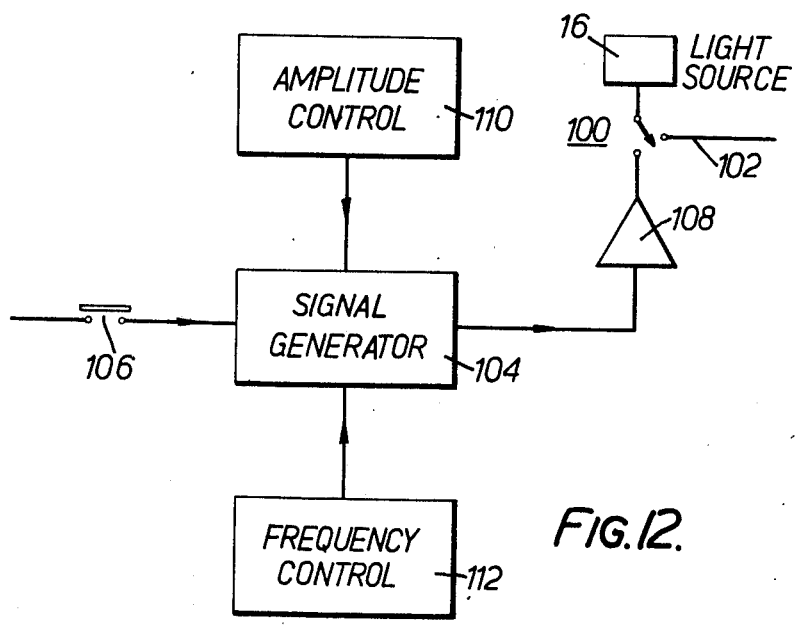
FIG. 12 is a block circuit diagram of the modified form of apparatus to be described with reference to FIGS. 8 to 11.

FIG. 12 shows apparatus for carrying out the measurement of modulation transfer function as described above. As shown the lamp 16 is fed via a switch 100 which can connect the lamp either to the circuitry shown in FIG. 3 (by means of a line 102) or to circuitry which will now be described.

The latter circuitry comprises a signal generator 104 which is energised from a suitable power source through a switch 106 and, when operative, produces a desired output — for example, sinusoidal or pulse form as shown in FIGS. 8 to 11. This output is fed to lamp 16 via an amplifier 108 and switch 100. Controls 110 and 112 enable the amplitude (with respect to a selected datum) and frequency of the output to be adjusted.

The circuitry of FIG. 12 can of course be constructed to be self-contained, that is, not sharing the lamp 16 with the circuitry of FIG. 3.

What is claimed is:

1. A method of testing vision, including the steps of producing randomly time-separated groups of visual stimuli each group consisting of a predetermined number of successive stimuli, each stimulus in a said group being separated from the next stimulus in that group by a controllable-length time interval, varying the length of each said controllable-length time interval, and assessing the minimum said controllable-length time interval for which the subject under test can discern the separate stimuli.

2. A method according to claim 1, in which each said group consists of a pair of visual stimuli.

3. A method according to claim 1, in which the stimuli are flashes of light.

4. A method according to claim 2, in which each visual stimulus occupies a small discrete portion of the subject's visual field, and including the steps of
providing a fixation mark for fixing the centre of the subject's visual field, and
varying the position, relative to the fixation mark, in which the said visual stimuli are presented.

5. A method according to claim 1, including the step of providing a predetermined level of background illumination for the subject's visual field during the repetition of the said visual stimuli.

6. A method according to claim 1, including the step of detecting pupillary response in the subject in order to assess the minimum said interval discernible.

7. A method according to claim 1, in which the step of producing each visual stimulus comprises the step of producing a first abrupt change in brightness level in a predetermined direction followed by a second change in brightness level in the opposite direction.

8. A method according to claim 7, in which each said first change in brightness level is an increase in brightness level, and in which each visual stimulus is spatially patterned.

9. A method according to claim 1, in which the step of producing each visual stimulus comprises the step of producing an abrupt change in spatial patterning followed by an abrupt change in the opposite direction.

10. A method according to claim 9, in which the spatial patterning is a pattern of different colors.

11. A method according to claim 9, including the step of preserving the mean spatial luminance presented to the subject substantially unaffected by the visual stimuli.

12. A method according to claim 1, in which the step of producing each visual stimulus comprises the step of producing an abrupt change in color followed by an abrupt change back again.

13. A method of testing vision, comprising the steps of
producing a visual stimulus of periodically varying intensity for a small discrete portion of a subject's visual field,
changing the amplitude of the intensity variations, and
assessing the minimum amplitude value for which the subject can discern the variations.

14. A method according to claim 13, including the steps of providing a fixaton mark for fixing the center of the subject's visual field, and varying the position, relative to the fixation mark, in which the said stimulus is presented.

15. A method according to claim 13, including the step of changing the frequency of the intensity variations.

16. A method according to claim 13, in which the intensity variations are in sinusoidal form.

17. A method according to claim 13, in which the intensity variations are variations with respect to a finite and constant mean level of intensity.

18. A method according to claim 13, in which the intensity variations are variations with respect to a zero level of intensity.

19. Apparatus for testing vision, including
visual stimulus means,
activating means connected to the visual stimulus means and operative to produce therefrom randomly time-separated groups of visual stimuli, each group consisting of a predetermined number of successive stimuli with each stimulus in a said group being separated from the next stimulus therein by a controllable-length time interval, and
control means connected to the activating means to vary the said controllable-length time intervals so as to enable the minimum said interval discernible by a subject under test to be assessed.

20. Apparatus according to claim 19, in which each said group consists of two stimuli.

21. Apparatus according to claim 19, in which the visual stimulus means is a light source and the activating means comprises means for flashing the light source.

22. Apparatus according to claim 19, in which the light source produces spatially patterned light.

23. Apparatus according to claim 19, including
fixation means for presenting a fixation mark to the subject for the subject's visual field, and
means for supporting the fixation means and the visual stimulus means for relative movement in the visual field,
the visual stimulus means being arranged to produce visual stimuli which occupy a small, discrete, portion of the visual field.

24. Apparatus according to claim 19, including means for testing pupillary response in the subject, whereby to detect the said interval.

25. Apparatus according to claim 19, in which the visual stimulus means includes electrically energizable light source means and the activating means comprises electrical energization means for energizing the light source means, and in which the control means comprises first electrical timing means having a predetermined time period for correspondingly controlling the energization means whereby to determine the time duration of each individual visual stimulus, and second electrical timing means having a predetermined time period for controlling the time separation of successive instants of initiation of the first timing means whereby to control the interval between successive visual stimuli.

26. Apparatus according to claim 25, in which the second timing means is electrically connected to be initiated in response to the end of the first time period, only, of the first timing means following a first initiation of the latter, and the second timing means is electrically connected to reinitiate the first timing means at the end of the time period of the second timing means.

27. Apparatus for testing vision including:
visual stimulus means,
activating means connected to the visual stimulus means and repetitively operative to produce therefrom a group of visual stimuli containing a predetermined number of successive stimuli, and
control means connected to the activating means to vary the time intervals between the stimuli in each group so as to enable the minimum interval discernible by a subject under test to be assessed;
the visual stimulus means comprising
first and second light sources each for producing light of a first predetermined color,
third and fourth light sources each for producing light of a second predetermined color, a patterned partial-mirror carrying a pattern of light reflecting strips and being light-transmitting between the strips, means mounting the first and third light sources to direct light towards one surface of the mirror whence it is reflected by the said strips in a predetermined direction, means mounting the second and fourth light sources to direct light towards the opposite surface of the said mirror whence it passes through the mirror between the said strips and in the said predetermined direction, the first and second predetermined colors beings selected whereby when all four light sources are producing light of substantially equal luminance, the composite beam of differently colored light proceeding in the said predetermined direction produces a third predetermined color but when the luminance of the light from the first and third light sources is given a step change in a predetermined direction and, simultaneously, the luminance of the light from the second and fourth light sources is given an equal step change in the opposite direction, the said composite beam produces a pattern of the first and second colors, the luminances of the light sources being connected to be controlled by the said control means whereby the said visual stimuli are produced by changes in the form of the said composite beam.

28. Apparatus for testing vision, comprising fixation means for fixating the subject's visual field, light source means for producing a small discrete visual stimulus in a portion of the visual field, means for altering the physical relationship between the fixation means and the light source means whereby to shift the small discrete visual stimulus to a different portion of the visual field, first control means for giving the visual stimulus a periodically varying intensity, and second control means for changing the amplitude of the intensity variations to assess the minimum amplitude value for which the subject can discern the variations.

29. Apparatus according to claim 28, including third control means for changing the frequency of the intensity variations.

30. A method of testing a human subject's vision, including the steps of providing a fixation mark for fixating the subject's visual field, providing a predetermined level of background illumination over the subject's visual field, presenting, at a first position relative to the fixation mark, randomly time-separated groups of visual stimuli each group consisting of two stimuli separated by a controllable-length time interval, carrying out a series of tests during which the lengths of the controllable-length time intervals are varied and the minimum controllable-length time interval for which the subject under test can discern the separate stimuli in each group is assessed, and presenting further said groups of visual stimuli at another position relative to the fixation mark, and carrying out another said series of tests thereat.

31. Apparatus for testing a human subject's vision, comprising fixation means for presenting a fixation mark to the subject for fixating the subject's visual field, means positioned relative to the fixation means for providing a predetermined level of background illumination for the subject's visual field, visual stimulus means arranged to produce visual stimuli which each occupy a small, discrete, portion of the visual field, means for supporting the fixation means and the visual stimulus means for relative movement whereby to move the visual stimulus means within the subject's visual field, activating means connected to the visual stimulus means and operative to produce therefrom randomly time-separated groups of visual stimuli each group consisting of a pair of stimuli separated by a controllable-length time interval, and control means connected to the activating means to vary the length of the controllable-length time intervals so as to enable the minimum said interval discernible by a subject under test to be assessed.

* * * * *